(12) United States Patent
Culbertson et al.

(10) Patent No.: US 6,512,054 B2
(45) Date of Patent: Jan. 28, 2003

(54) SYNTHESIS OF FREE RACDICAL OR VISIBLE LIGHT CURABLE ACID CONTAINING POLYMERS

(75) Inventors: Bill M. Culbertson, Columbus, OH (US); Scott R. Schricker, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 09/765,099

(22) Filed: Jan. 17, 2001

(65) Prior Publication Data

US 2002/0010227 A1 Jan. 24, 2002

Related U.S. Application Data

(60) Provisional application No. 60/176,855, filed on Jan. 19, 2000.

(51) Int. Cl.[7] .............................. A61K 6/083; C08F 8/30; C08J 3/28; C08K 3/34; C08L 31/06; C08L 33/02
(52) U.S. Cl. .................... 525/279; 525/303; 525/329.5; 525/329.6; 525/329.7; 525/375; 523/115; 523/116; 524/443; 524/555; 522/152; 522/154; 106/35; 433/228.1
(58) Field of Search ................................. 525/279, 303, 525/329.5, 329.6, 329.7, 375; 523/115, 116; 524/443, 555; 522/152, 154; 106/35; 433/228.1

(56) References Cited

U.S. PATENT DOCUMENTS 3,758,629 A     9/1973  Thill
4,056,502 A    11/1977  Gross
4,131,724 A    12/1978  Radlmann et al.
4,608,419 A     8/1986  Droman et al.
5,130,347 A     7/1992  Mitra
5,990,226 A    11/1999  Arita et al.
6,136,885 A    10/2000  Rusin et al.

OTHER PUBLICATIONS

"Functionalization of Poly(acrylic acid) with Cyclic Imino Ethers for Biomaterials and Coatings Applications" by Schricker, et al., Polymer Preprints Aug. 1999, pp 181–182.
"A One Pot, Two Step Reaction for the Synthesis of VLC Acidic Polymers for Resin Modified Glass Ionomers" by Schricker, et al, Polymers for Advanced Technologies, 12, pp. 387–390 (Jun. 2001).

Primary Examiner—D. R. Wilson
(74) Attorney, Agent, or Firm—Calfee, Halter & Griswold LLP

(57) ABSTRACT

Methods for preparing free radical or visible light curable (VLC) acid-containing polymers in an aqueous solution are provided. In one embodiment, the method comprises reacting polymers having reactive carboxylic acid groups with a methacrylated oxazoline or oxazine, collectively referred to hereafter as "methacrylated unsaturated cyclic imino ethers," in an aqueous solution at a temperature of from about 50° C. to about 75° C. In another embodiment, the method comprises an additional step of preparing the carboxylic acid-containing polymer in an aqueous solution and then reacting the carboxylic acid-containing polymer with the methacrylated cyclic imino ether in the aqueous solution. The present invention also relates to free radical or VLC acid-containing polymers, and dental restoratives that comprise such polymers. Methods of attaching an oxazoline or oxazine to a carboxylate group on a polymer in an aqueous solution are also provided.

26 Claims, 1 Drawing Sheet

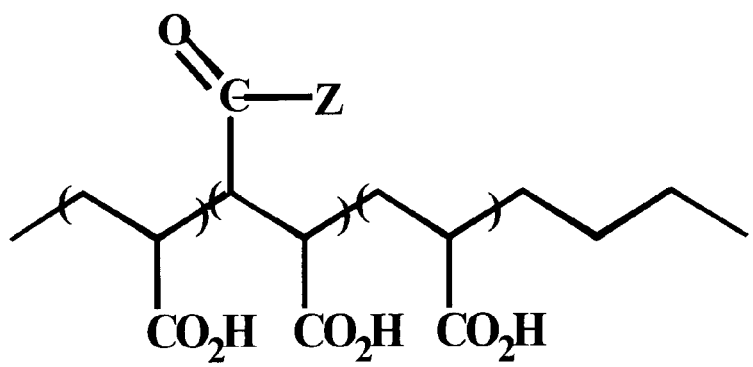

B

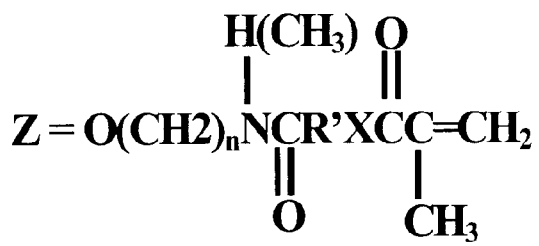

n = 2 or 3

X = O, NH, or NR (R is an alkyl chain; i.e., methyl, ethyl, propyl, butyl, pentyl, hexyl, heptyl, octyl, nonyl, decyl, undecyl or dodecyl).

R' = aliphatic residue (i.e., straight or branched alkane, alkene or alkyne of from 1-12 C atoms and 0-5 heteroatoms which are O, N, S, or combinations thereof. Sidechain H atoms are unsubstituted, or substituted with an alkyl group, ester or amide) or an aromatic residue (i.e., a 5 or 6 member ring fulfilling 4n+2 requirement. Rings of 6 members are comprised of either C atoms or C atoms plus heteroatoms. Rings of 5 members are comprised of C atoms plus heteroatoms, wherein H atoms on the ring are unsubstituted or substituted with an alkyl group, ester or amide).

SYNTHESIS OF FREE RACDICAL OR VISIBLE LIGHT CURABLE ACID CONTAINING POLYMERS

CROSS REFERENCE TO RELATED APPLICATIONS

This application claims priority from U.S. Provisional Application No. 60/176,855, filed Jan. 19, 2000.

This invention was made, at least in part, with government support under National Institutes of Health Grant No: DE 11682-03 awarded by the National Institute of Dental and Craniofacial Research. The U.S. government has certain rights in the invention.

BACKGROUND OF THE INVENTION

An important type of modern dental restorative consists of an organic polymer containing carboxylic acid groups combined with an inorganic filler material which is normally a calcium fluoroaluminosilicate glass powder. Cations within the glass react with the ionized carboxylic acid groups of the polymer to form salt-bridges. Such salt bridge formation results in the polymer/glass mixture becoming a hardened, insoluble matrix. Important properties of such dental restoratives are high levels of strength, toughness and wear resistance, and also minimal shrinkage.

The polymer component of the restorative is perhaps most critical for imparting high quality mechanical and minimal shrinkage properties to the dental restorative. One method of improving both the mechanical and shrinkage properties of the polymer has been to graft a methacrylate onto the polymer backbone. Such methacrylates are attached to the polymer backbone via the carboxylate moieties. Examples of graftable methacrylates which have been used for this purpose include 2-isocyanatoethyl methacrylate (IEM) and glycidyl methacrylate (GM).

Acidic polymers which have methacrylates grafted onto their backbone are visible light-curable (VLC) polymers. Typically, the acidic polymer is a copolymer of acrylic acid with itaconic acid. However, copolymers of acrylic acid and maleic acid are also known. The polyacid is made visible light-curable by the reaction of isocyanoethyl methacrylate (IEM).

The reaction of an acid-containing polymer (structure I below shows a polymer of acrylic acid and itaconic acid) with IEM (structure II below) to give the VLC polymer (structure III below) is performed in the organic solvent tetrahydrofuran (THF).

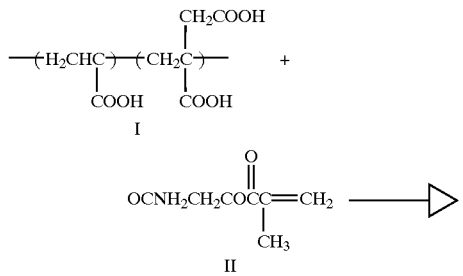
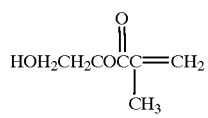

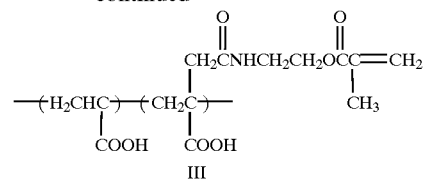

In addition to the VLC polymer, the other major components of the dental restorative, i.e., the resin modified glass ionomer (RMGI), are a basic aluminofluorosilicate glass, 2-hydroxyethyl methacrylate (HEMA), water and a visible light polymerization initiator. The structure of HEMA is shown below (structure IV).

$$HOH_2CH_2COCC\!\!=\!\!CH_2 \atop \underset{CH_3}{|}$$

IV

The RMGI is a dual cure system which involves (1) an acid-base reaction between the ionized carboxylate groups of the polymer and the basic glass, and (2) a copolymerization of the methacrylate groups present on the major components, i.e., the methacrylate groups which are pendant on the VLC polymer, the HEMA methacrylate groups, and in some cases, methacrylate groups which are attached to the glass. A strong visible-light source is used to catalyze formation of the covalent bonds. Hardening of such dental restoratives occurs due to the two types of bonding. Some products also contain a redox initiator system which will further cure the methacrylate groups after the light source is removed. These are referred to as tri-cure systems.

Unfortunately, IEM, one of the methacrylates which is commonly used to prepare the VLC polymer, is a highly toxic liquid with significant regulatory barriers to its manufacture and distribution on a large scale. IEM also presents health and environmental concerns. In addition, IEM is very expensive and, thus, adds significantly to the cost of preparing VLC polymers. Reactions which employ GM as the methacrylate are high temperature reactions that are conducted at temperatures in excess of 90° C., and can lead to premature polymerization of methacrylate groups.

Accordingly, it is desirable to have new methods which do not utilize IEM or GM to prepare the VLC polymers which are used in resin modified glass ionomers.

SUMMARY OF THE INVENTION

The present invention provides new methods for preparing free radical or visible light curable (VLC) acid-containing polymers in an aqueous solution. Such polymers are prepared from a polymer backbone containing reactive carboxylic acid groups. In one embodiment of the invention, the method of making the free-radical or visible light curable polymer comprises reacting polymers having carboxylic acid groups with a methacrylated oxazoline or oxazine, collectively referred to hereafter as "methacrylated unsaturated cyclic imino ethers," in an aqueous solution at a temperature of from about 50° C. to about 75° C. In another embodiment, the method comprises an additional step of preparing the carboxylic acid-containing polymer in an aqueous solution and then reacting the carboxylic acid-containing polymer with the methacrylated cyclic imino ether in the aqueous solution (i.e., one-pot, two-step reaction). A general scheme for reaction of a copolymer of acrylic acid and itaconic acid monomeric units (structure V) with an N-oxazoline (structure VI) to produce a VLC polymer (structure VII) is shown below.

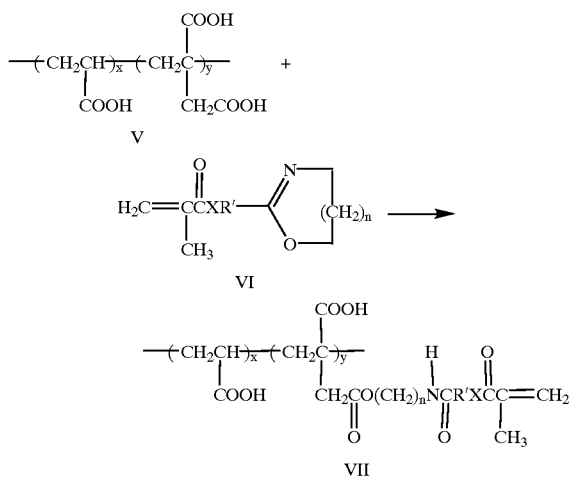

n=2 or 3
X=O, NH or NR (R=alkyl residue)
R'=aliphatic and/or aromatic residues, possibly containing heteroatoms such as N, O or S The present invention also relates to VLC acid-containing polymers that are made in accordance with the present methods, and dental restoratives, or RMGI, that comprise such polymers.

The present invention also relates to a method of attaching an oxazoline or oxazine to a carboxylate group on a polymer in an aqueous solution.

BRIEF DESCRIPTION OF THE FIGURES

FIG. 1 is a schematic representation of a VLC polymer of the present invention.

DETAILED DESCRIPTION OF THE INVENTION

The present invention provides new methods for preparing VLC acid-containing polymers in an aqueous solution. Such methods comprise reacting a carboxylic acid-containing polymer with a methacrylated unsaturated cyclic imino ether without substantially cross-linking the polymer. The present invention also provides new VLC polymers, that could not be made using prior synthetic methods.

Carboxylic acid-containing polymers used in the synthesis of the VLC polymers include any acid-containing polymer that is soluble in a solution comprised of water and alcohol. Such polymers are either linear, branched, hyperbranched, star, or dendritic. Such polymers or co-polymers are made from monomers or co-monomers such as, but not limited to, acrylic acid, methacrylic acid, itaconic acid, N-acryloyl and N methacryloyl amino acids, maleic acid, and citraconic acid. Examples of such polymers and co-polymers are poly(acrylic acid), poly(methacrylic acid), poly(maleic acid) poly(itaconic acid) poly(acrylic acid-co-itaconic acid), and poly(acrylic acid-co-maleic acid). Suitable polymers are homopolymers, such as for example, poly(acrylic acid), poly(methacrylic acid), poly(maleic acid) and poly(itaconic acid). Preferably, the polymer is a co-polymer formed from monomers of acrylic acid and itaconic acid or acrylic acid and maleic acid. Such polymers are commercially available. Preferably, the polymer or co-polymer is made as described below.

To produce VLC polymers from the polymer backbone described above, such carboxylic acid-containing polymers are mixed with a methacrylated unsaturated cyclic imino ether, preferably a methacrylated oxazoline or oxazine. The general structure of an unsaturated oxazoline and oxazine that is used in this method is shown below (structure VIII);

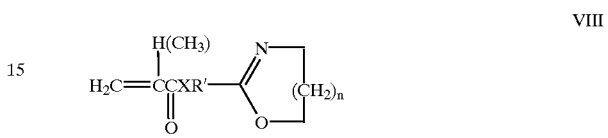

wherein n is 2 or 3; X is O, NH, or NR; wherein R is an alkyl chain selected from the group consisting of methyl, ethyl, propyl, butyl, pentyl, hexyl, heptyl, octyl, nonyl, decyl, undecyl, and dodecyl; and R' is an aliphatic residue or an aromatic residue. The aliphatic residue is a straight or branched alkane, alkene, or alkyne carbon chain which comprises from 1 to 12 carbon atoms and from 0 to 5 heteroatoms selected from the group consisting of O, N, S, and combinations thereof. The hydrogen atoms on the chain are unsubstituted or substituted with an alkyl group, an ester, or an amine. The aromatic residue is a 6 membered ring or a 5 membered ring which fullfills the 4n+2 rule, which is known in the art. The 6 membered ring comprises carbon atoms or a combination carbon atoms and heteroatoms selected from the group consisting of O, N, and S. The 5 membered ring comprises a combination of carbon atoms and heteroatoms selected from the group consisting of O, N, and S. Examples of the 6 membered ring are benzene and pyridine rings. Examples of the 5 membered ring are pyrrole, thiophene, and furan. The hydrogen atoms on the ring structure are unsubstituted or substituted with an alkyl group, an ester, or an amide.

The methacrylated unsaturated cyclic imino ether may be either an aliphatic oxazoline or oxazine or an aromatic oxazoline or oxazine. Because of their solubility in aqueous solutions, aromatic oxazolines or oxazines are preferred. One example of a suitable methacrylated aliphatic oxazoline is shown below as structure IX.

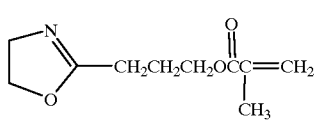

Examples of suitable methacrylated aromatic oxazolines or oxazines are shown below as structures X, XI, XII and XIII.

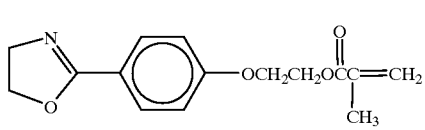

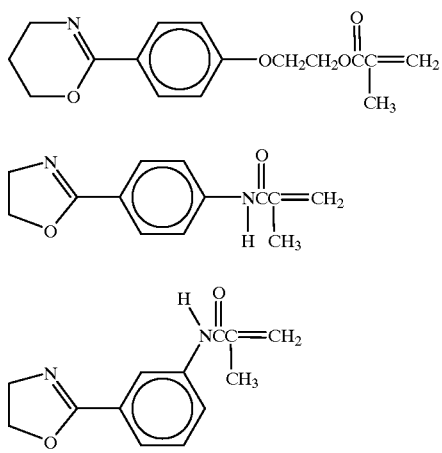

In structures XII and XIII above, an oxygen is replaced by a nitrogen. Structures X depicts a methacrylated oxazoline. Structure XI depicts a methacrylated oxazine. Structures XII and XIII depict oxazolines substituted with methacrylamide-containing groups.

In order to make VLC polymers with the reactants described above, the methacrylated unsaturated cyclic imino ether is added to a solution containing the carboxylic acid-containing polymers. The polymer is first dissolved in an aqueous solution which preferably comprises water and an alcohol. Examples of suitable alcohols include, but are not limited to, methanol, ethanol, butanol, and propanol. In a preferred embodiment, the alcohol is isopropanol. Preferably the aqueous solution is comprised of from about 5% to about 95% water and from about 95% to about 5% alcohol, more preferably from about 40% to about 60% water and from about 60% to about 40% alcohol.

The methacrylated unsaturated cyclic imino ether and polymer are present in the reaction mixture at a molar ratio of 5–25%, preferably of 10–20%, more preferably of 15%, based on carboxylic acid groups. The solution is then heated to a temperature of from about 50° C. to about 75° C., preferably from about 60° C. to about 70° C., followed by the addition of the methacrylated unsaturated cyclic imino ether to the heated solution. The reaction requires no catalyst. Following completion of the reaction, which normally takes from 2 to 8 hours, the VLC acid-containing polymer is recovered from the solution, typically by freeze drying the solution and dissolving in methanol, followed by precipitation with ethyl acetate or ether. Such method can also be used to attach non-methacrylated oxazolines and oxazines to carboxylate groups on any polymer which is soluble in an alcohol-water solution.

In another embodiment, the method further comprises a prior step of synthesizing the carboxylic acid-containing polymer in an aqueous solution. The polymer may be a homopolymer or co-polymer. The desired monomers, such as for example, acrylic acid and itaconic acid, are added to the aqueous solution at a desired ratio and polymerized. The monomers are dissolved in a water solution with 0–5% isopropanol and either a thermal (such as potassium persulfate) or visible light initiator (such as diphenyl iodonium chloride) is added at a concentration from about 0.001 to 5 mole percent. For the thermal initiator, the solution is heated to 85° C., or the appropriate degradation temperature for the initiator, for 6–36 hours. For the visible light initiator, the solution is irradiated with a strong visible light source for 4–36 hours or until the polymerization is complete. The polymer can then be isolated by standard freeze drying techniques in which water vapor is removed under vacuum, leaving only the solid polymer residue. The solid polymer can be dissolved in pure methanol. The methanol solution can then be combined with a large excess of ethyl acetate which precipitates the polymer.

Because many carboxylic acid-containing polymers can be synthesized in aqueous media, this leads to the ability to synthesize the VLC polymers in a one-pot, two-step procedure starting from monomers used to synthesize the polymer backbone. Such synthesis avoids the use of an organic solvent such as tetrahydrofuran and other organic solvents which are used in the more traditional, high-temperature synthesis of VLC polymers. The reaction below depicts the one-pot, two-step reaction, but the modification of carboxylic acid-containing polymers by cyclo-imino ethers with methacrylate residues as a separate reaction (the second step of the overall reaction below) is also part of the invention.

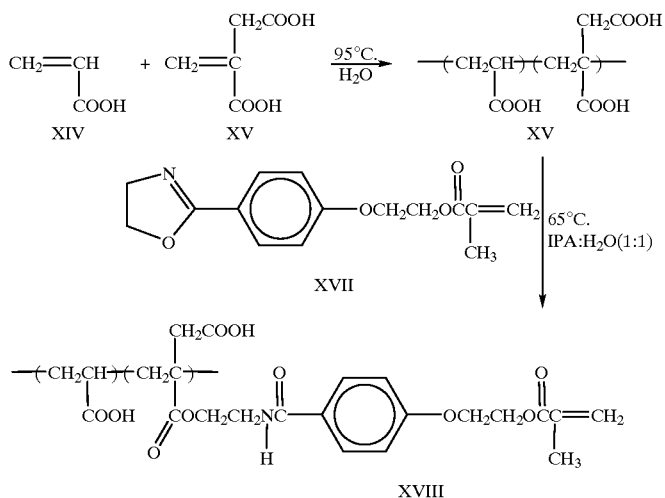

In the above reaction, acid-containing monomers, such as but not limited to, acrylic acid (structure XVII) and itaconic acid (structure XV) are polymerized in water to give the co-polymer (structure XVI). To this reaction mixture, enough isopropanol (labeled "IPA" in the figure) is added to create a 1:1 mixture of water and isopropanol. The methacrylated oxazoline (structure XVI) is added at 65° C. and the reaction mixture is allowed to stir for four hours. After the VLC polymer (structure XVIII) is isolated and purified, it can then be formulated with various resins and glass powders for use in biomaterials. Typically, the VLC polymer is isolated by precipitation.

The polymers of the present invention may be combined with a glass powder, preferably a calcium-fluoroaluminosilicate type (CaFAlSi) glass powder, to make an organic-inorganic hybrid composite, referred to as a resin modified glass ionomer (RMGI).

To make the RMGI, VLC polymers are dissolved in a mixture of water and 2-hydroxy ethyl methacrylate (HEMA). HEMA is a polymerizable solvent and co-reactant used for resin-modified glass ionomer (RMGI) formulations. The water:HEMA mixture is preferably from 20% to 50% HEMA. The VLC polymer can be dissolved at the 50% level in water:HEMA and then can be combined with $CaFAlSiO_2$ glass powder to give a mixture that is between 50–80% by weight of glass. The resulting RMGI dental restorative, which is a homogeneous, paste-like mixture, is applied to the dental area in need of restoration. A strong visible light source can be used to catalyze formation of covalent bonds via a free radical reaction. In such case, hardening or curing occurs both by crosslinking of the organic polymer matrix and the acid-base reaction of the carboxylate $CO_2^-$ anions and the $Ca^{++}$ or $Al^{+++}$ cations from the glass.

EXAMPLES

The following examples are for purposes of illustration only and are not intended to limit the scope of the invention as defined in the claims, which are appended hereto.

Example 1
Preparation of VLC polymer by reacting poly(acrylic acid) (PAA) with a vinyl-substituted oxazoline (structure XVII)

3.0 g (0.0416 mols based on acrylic acid) of poly(acrylic acid) Mw=2,000 was dissolved in 15 mL of water. To this, 15 mL of isopropanol was added and the solution was warmed to 65° C. To the heated solution, 2.28 g (0.0083 mols) of methacrylated oxazoline (structure XVII) was added and the reaction flask was fitted with a reflux condenser. The reaction mixture was homogeneous and was allowed to stir for four hours. The resulting methacrylated polymer was isolated from the reaction mixture by precipitation with water. The solid was dissolved in tetrahydrofuran (THF) and precipitated with ether (2X). The structure was confirmed by NMR.

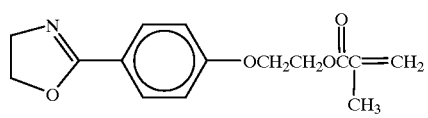

XVII

Example 2
Crosslinking reaction of the polymer of example 1 with acrylic acid

One hundred mg of the methacrylated poly(acrylic acid) of example 1 and 50 mg of the free radical polymerization initiator, benzoyl peroxide (BPO), were dissolved in a solution of 1 ml of acrylic acid and 1 ml of water in a test tube. As a control, 50 mg of BPO was dissolved in a solution of 1 ml of acrylic acid and 1 ml of water. Both solutions were heated overnight at 80° C. The solution containing the methacrylated poly(acrylic acid) gave an insoluble mass, indicating that the methacrylate is attached to the backbone of the polymer, while the other test tube remained a solution.

Example 3
Crosslinking reaction of the polymer of example 1 with methacrylic acid One hundred mg of the methacrylated poly(acrylic acid) and 50 mg of BPO were dissolved in a solution of 1 ml of methacrylic acid and 1 ml of water in a test tube. As a control, 50 mg of BPO was dissolved in a solution of 1 ml of methacrylic acid and 1 ml of water. Both solutions were heated overnight at 80° C. The solution containing the methacrylated poly(acrylic acid) gave an insoluble mass while the other test tube remained a solution.

Example 4
One-pot synthesis of poly(acrylic acid-co-itaconic acid) and subsequent reaction with vinyl-substituted oxazoline (structure XVII) to give a VLC acid-containing polymer Mixture A of potassium persulfate (0.134 g) in 15 mL of distilled water was stirred under nitrogen atmosphere for 30 min to remove dissolved oxygen. Mixture B of acrylic acid (5.04 g, 70 mmol) and itaconic acid (3.90 g, 30 mmol) in 10 ml of distilled water and 2 mL of isopropanol was placed in an addition funnel. Mixture C of potassium persulfate (0.134 g) in 5 mL of distilled water was placed in another addition funnel. The reaction was heated to 95° C., and every five minutes, ¹⁄₁₀ of mixture B and ¹⁄₁₀ of mixture C was added to mixture A. The reaction was allowed to proceed for 18 hours and then cooled to 60° C. 2,6-di-tert-butyl-4-methylphenol Inhibitor (BHT) (1% w/w) was added to the reaction mixture to prevent premature polymerization. Then, a warm solution of structure XVII (5.369 g) in isopropanol was added to the reaction mixture and stirred at 60° C. for 18 hours. The reaction was cooled to room temperature and poured into water. The viscous solid was collected, dissolved in THF, precipitated with ether (2X) and dried in a vacuum oven. Yield from the reaction was 10.87 g (76%). The product was characterized by NMR and FT-IR. The modified polymer is soluble in water:HEMA 1:1 at 50 wt percent.

Example 5
One-pot, two-step synthesis of poly(acrylic acid-co-itaconic Acid)-based VLC Polymer, formulation into an RMGI and physical testing of the RMGI A mixture of 0.402 g (0.0015 moles) of potassium persulfate, $K_2S_2O_8$, in 52 ml distilled water, was placed in a three-necked flask with a mechanical stirrer and two addition funnels, stirred under nitrogen purge for 30 min to remove dissolved oxygen and then heated to 95° C. Solution A: 15.13 g (0.210 moles) of acrylic acid, 11.71 g (0.09 moles) of itaconic acid, 26 ml of $H_2O$ and 5.2 ml of isopropanol, was placed in an addition funnel attached to the main reaction flask. Solution B: 15.6 ml of $H_2O$ and 0.402 g (0.0015 moles) of $K_2S_2O_8$ was placed in a separate addition funnel attached to the main reaction flask. ¹⁄₂₀ of both solution A and B was added every five minutes until addition was complete.

After FT-IR showed that the carbon-carbon double bond (C=C) peaks of the monomers (acrylic acid and itaconic acid) had disappeared, 20.398 g of the polymer solution was cooled to 60° C., followed by adding a mixture of 1% butylated hydroxytoluene and 2.605 g (0.0095 moles) of OPEM (a methacrylated functionalized aromatic oxazoline, shown as structure XVII in this application, 15% mole fraction) in 5 ml of isopropanol. The stirred reaction mixture was continued at 60° C. for 8 hours and cooled down to room temperature.

A large excess of distilled water was used to precipitate the polymer, which was then dissolved in tetrahydrofuran and precipitated in ethyl ether (2X). The polymer was collected, washed with ethyl ether several times and dried overnight under vacuum at 35° C. $^1$H NMR (500 MHz, DMSO-d$_6$): δ 1.2–1.6 ppm (m, 4H); 1.7 ppm (m, 3H); 1.8 ppm (s, 3H;) 1.9–2.3 ppm (m, 8H); 3.24 ppm (t, 2H); 3.6 ppm (t, 3H); 4.35–4.47 ppm (m, 4H); 5.7 ppm (s, 1H); 6.0 ppm (s, 1H); 7.1 ppm (d, 2H); 8.0 ppm (d, 2H). $^{13}$C NMR (500 MHz, DMSO-d$_6$): δ 18.3 ppm; 39.3 ppm; 40.0 ppm (broad peak); 61.6 ppm; 63.2 ppm; 66.5 ppm; 67.4 ppm; 114.8 ppm; 122.1 ppm; 126.5 ppm; 132.2 ppm; 136.0 ppm; 162.7 ppm; 165.6 ppm; 166.8 ppm; 173.2 ppm; 176.2 ppm; 177.3 ppm. These NMR data confirmed the presence of the methacrylate group on the polymer backbone.

The VLC polymer was then formulated to evaluate its use in an RMGI. The polymer was soluble in a 1:1 water:HEMA mixture at the 50% level and could now be formulated in an RMGI. Three different liquid phases, A, B and C, were formulated as shown in Table 1. These three formulations were then mixed with the glass of Fuji II LC (using a powder/liquid ratio of 3/1) and compared to Fuji II LC as shown in Table 2. The three liquid formulations were then mixed with the Vitremer Tricure glass (using a powder/liquid ratio of 2.5/1) and compared to the standard Vitremer as shown in Table 3. Specimens of different sizes were made for each physical test (see below). A COE-Lite (Model 4000, Imperial Chemical Industries PLC, Maccles Field, Cheshire, UK) was used as a light source to cure the specimens for 4 min.

TABLE 1

Compositions of Copolymer Solution (wt. %)

| System | Polymer | HEMA | Water | CQ | DC | PS |
|---|---|---|---|---|---|---|
| A | 52.5 | 18 | 29.5 | 0.5 | 1.4 | 0.1 |
| B | 55 | 15 | 30 | 0.5 | 1.4 | 0.1 |
| C | 58 | 12 | 30 | 0.5 | 1.4 | 0.1 |

CQ: dl-camphorquinone
DC: diphenyliodonium chloride
PS: potassium persulfate
HEMA: 2-hydroxyethyl methacrylatye

TABLE 2

Mechanical Properties of Copolymer Formulations with Fuji II Powder

| System | P/L Ratio | CS (SD) MPa | DTS (SD) Mpa |
|---|---|---|---|
| Fuji II LC | 3.0:1 | 305.45 (5.33) | 42.06 (3.83) |
| A | 3.0:1 | 259.74 (12.67) | 38.94 (1.52) |
| B | 3.0:1 | 283.49 (13.34) | 44.67 (2.93) |
| C | 3.0:1 | 299.41 (7.66) | 45.83 (1.66) |

TABLE 3

Mechanical Properties of Copolymer Formulations with Vitremer Tricure Powder

| System | P/L Ratio | CS (SD) MPa | DTS (SD) Mpa |
|---|---|---|---|
| Vitremer | 2.5:1 | 247.89 (3.35) | 45.25 (3.33) |
| A | 2.5:1 | 214.99 (5.69) | 40.38 (2.06) |
| B | 2.5:1 | 222.12 (5.35) | 41.27 (2.59) |
| C | 2.5:1 | 224.21 (6.34) | 43.26 (1.51) |

Physical testing of the RMGI formulations was performed as described below. A universal testing machine (Instron Model 4204, Instron Corp., Canton, Mass., USA) was used to test the compressive strength (CS) and diametral tensile strength (DTS) at a crosshead speed of 0.5 mm/min.

For CS testing, six cylindrical specimens with 4 mm in diameter by 8 mm in length were prepared in glass tubing, using the help of a pressure fixture to remove air bubbles from the uncured paste. After 1 hr in 100% humidity at 37° C., the test specimens were removed from the glass tubing and conditioned in distilled water at 37° C. for 7 days, prior to testing. The compressive strength of each specimen was determined by loading the flat ends of the specimens on the Intron Universal Testing Machine. The compressive strength was determined by the formula: $CS=P/(\pi R)$, where P=the load at fracture, and R=the radius of the sample cylinder.

For DTS testing, six cylindrical specimens 4 mm in diameter by 2 mm in thickness were prepared in glass tubing, using the help of a pressure fixture to remove air bubbles from the uncured paste. After 1 hr in 100% humidity at 37° C., the test specimens were removed from the glass tubing and conditioned in distilled water at 37° C. for 7 days, prior to testing. The diametral tensile strength of each specimen was determined by loading the specimens with radial axis parallel to the load. The DTS was calculated using the formula: $DTS=2P/(\pi DT)$, where P=the load at fracture, D=the diameter of the cylinder, and T=the thickness of the cylinder.

The results show that OPEM (structure XVII) has the potential to replace IEM in adding a methacrylate functionality to a polyacid. The results for the Fuji II light cure system were better than the results for the Vitremer system.

What is claimed is:

1. A method for preparing a free radical or visible light curable acid-containing polymer wherein said method comprises:

a) reacting a carboxylic acid-functional polymer with an oxazoline or a 5,6-dihydro-1,3oxazine, wherein the oxazoline or the 5,6-dihydro-1,3oxazine has a 2-substituent, wherein the 2-substituent comprises an acrylate, a methacrylate, an acrylamido, or a methacrylamido group, in a aqueous solution, at a temperature of from about 50° C. to about 75° C. to provide said free radical or visible light curable acid-contaning polymer; and b) recovering said free-radical or visible light curable acid-containing polymer from the reaction mixture.

2. The method of claim 1 wherein the oxazoline or the 5,6-dihydro-1,3-oxazine has the following structure:

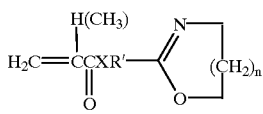

wherein n is 2 or 3;

X is O, NH, or NR, wherein R is an alkyl chain selected from the group consisting of methyl, ethyl, propyl, butyl, pentyl, hexyl, heptyl, octyl, nonyl, decyl, undecyl, and dodecyl;

R' is an aliphatic residue or an aromatic residue;

wherein the aliphatic residue is a straight or branched alkane, alkene, or alkyne carbon chain which comprises from 1 to 12 carbon atoms and from 0 to 5 heteroatoms selected from the group consisting of O, N, S, and combinations thereof, and wherein the carbon atoms on said chain are unsubstituted or substituted with an alkyl group, an ester, or an amide; and wherein the aromatic residue is a 6 membered ring or 5 membered ring which fullfills the 4n+2 rule, wherein said 6 membered ring comprises carbon atoms or a combination of carbon atoms and heteroatoms, wherein said 5 membered ring comprises a combination of carbon atoms and heteroatoms; and wherein the carbon atoms on said ring are unsubstituted or substituted with an alkyl group, an ester, or an amide.

3. The method of claim 1 wherein the aqueous solution comprises water and an alcohol.

4. The method of claim 3 wherein the alcohol is selected from the group consisting of isopropanol, methanol, ethanol, butanol, propanol, and combinations thereof.

5. The method of claim 1 wherein the carboxylic acid-functional polymer is homopolymer formed from a monomer selected from the group consisting of acrylic acid, itaconic acid, maleic acid, methacrylic acid, or a copolymer formed from 2 or more of said monomers.

6. The method of claim 1 wherein the oxazoline has the following structure:

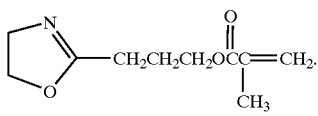

7. The method of claim 1 wherein the oxazoline or the 5,6-dihydro-1,3-oxazine has one of the following structures:

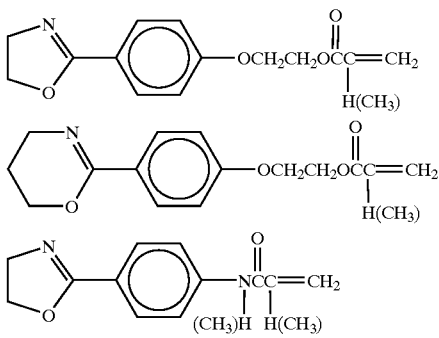

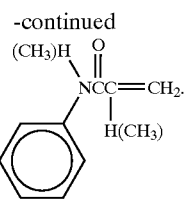

8. A free radical or visible light curable polymer produced by the method of claim 1.

9. The free radical or visible light curable polymer of claim 8 wherein said polymer has the following structure:

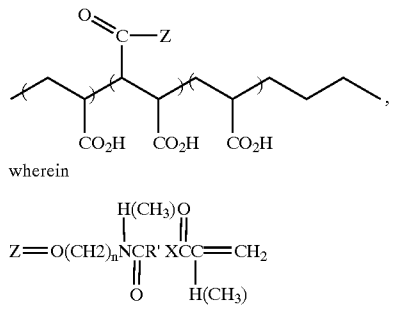

wherein n is 2 or 3;

X is O, NH, or NR, wherein R is an alkyl chain selected from the group consisting of methyl, ethyl, propyl, butyl, pentyl, hexyl, heptyl, octyl, nonyl, decyl, undecyl, and dodecyl;

R' is an aliphatic residue, or an aromatic residue, or a combination of an aliphatic residue and an aromatic residue;

wherein the aliphatic residue is a straight or branched alkane, alkene, or alkyne carbon chain which comprises from 1 to 12 carbon atoms and from 0 to 5 heteroatoms selected from the group consisting of O, N, S, and combinations thereof, and wherein the carbon atoms on said chain are unsubstituted or substituted with an alkyl group, an ester, or an amide; and wherein the aromatic residue is a 6 membered ring or 5 membered ring which fullfills the 4n+2 rule, wherein said 6 membered ring comprises carbon atoms or a combination of carbon atoms and heteroatoms, wherein said 5 membered ring comprises a combination of carbon atoms and heteroatoms; and wherein the carbon atoms on said ring are unsubstituted or substituted with an alkyl group, an ester, or an amide.

10. The free radical or visible light curable polymer of claim 9 wherein R' is an aliphatic residue.

11. The free radical or visible light curable polymer of claim 9 wherein R' is an aromatic residue.

12. The free radical or visible light curable polymer of claim 8 wherein the polymer comprises:

(a) a backbone comprising a plurality of monomeric units comprising carboxylic acids, wherein said monomeric units are selected from the group consisting of acrylic acid, methacrylic acid, maleic acid, itaconic acid, and combinations thereof; and (b) pendant groups comprising acrylate, methacrylate, acrylamido, or methacrylamido, attached to a plurality of the carboxylic acid groups.

13. The polymer of claim 12 wherein the backbone comprises monomeric units of acrylic acid and itaconic acid or acrylic acid and maleic acid.

14. A dental restorative comprising the free radical or visible light curable polymer of claim 9 and an inorganic filler.

15. The dental restorative of claim 14 wherein the inorganic filler is a basic aluminofluorosilicate glass, and the dental restorative further comprises 2-hydroxyethyl methacrylate and a free radical or visible light polymerization initiator.

16. A method for preparing a free radical or visible light curable acid-containing polymer wherein said method comprises:
   a) polymerizing carboxylic acid-functional monomeric units or co-monomeric units in an aqueous solution to provide an aqueous solution comprising a polymer comprising said monomeric or co-monomeric units;
   b) reacting the polymer of step (a) with an oxazoline or a 5,6-dihydro-1,3-oxazine, wherein the oxazoline or the 5,6-dihydro-1,3-oxazine has a 2-substituent, wherein the 2-substituent comprises an acrylate, a methacrylate, an acrylamido, or a methacrylamido group, in said aqueous solution at a temperature of from about 50° C. to about 75° C. to provide said free radical or visible light curable polymer; and
   c) recovering said free radical or visible light curable polymer from said acqueous solution.

17. The method of claim 16 wherein said monomeric and co-monomeric units comprise acrylic acid, maleic acid, itaconic acid, methacrylic acid, citraconic acid, N-acryloyl amino acids, N-methacryloyl amino acids, or combinations of said acids.

18. A method of reacting an oxazoline or a 5,6-dihydro-1,3-oxazine, wherein the oxazoline or oxazine has a 2-substituent, wherein the 2-substituent comprises an aromatic residue or an aliphatic residue, with a polymer comprising carboxylic acid groups, without substantially crosslinking the polymer; the method consisting of:
   a) providing an aqueous solution containing said polymer,
   b) then reacting the polymer of step (a) with the oxazoline or oxazine in said aqueous solution at a temperature of from about 50° C. to about 75° C. to provide a polymer having the aliphatic residue or an aromatic residue attached thereto;
wherein the aliphatic residue is a straight or branched alkane, alkene, or alkyne carbon chain which comprises from 1 to 12 carbon atoms and from 0 to 5 heteroatoms selected from the group consisting of O, N, S, and combinations thereof, and wherein the carbon atoms on said chain are unsubstituted or substituted with an alkyl group, an ester, or an amine; and
wherein the aromatic residue is 6 membered ring or 5 membered ring which fullfills the 4n+2 rule, wherein said 6 membered ring comprises carbon atoms or a combination carbon atoms and heteroatoms, wherein said 5 membered ring comprises a combination of carbon atoms and heteroatoms; and
wherein the carbon atoms on said ring are unsubstituted or substituted with an alkyl group, an ester, or an amide; and
   c) recovering said polymer from the aqueous solution.

19. The method of claim 18 wherein the aqueous solution comprises water and an alcohol.

20. The method of claim 19 wherein the alcohol is selected from the group consisting of isopropanol, methanol, ethanol, propanol, butanol and combinations thereof.

21. The method of claim 19 wherein the aqueous solution comprises from about 5% to about 95% water and from about 95% to about 5% alcohol.

22. The method of claim 19 wherein the aqueous solution comprises from about 40% to about 60% water and from about 60% to about 40% alcohol.

23. A method for preparing a free radical or visible light curable acid-containing polymer wherein said method comprises:
   a) reacting a carboxylic acid-functionalized polymer with an oxazoline or a 5,6-dihydro-1,3-oxazine comprising a free radical polymerizable vinyl substituent at the 2-position in an aqueous solution at a temperature of from about 50° C. to about 75° C. to provide said free radical or visible light curable acid-containing polymer, wherein the free radical polymerizable vinyl substituent is selected from the group consisting of acrylate, methacrylate, acrylamido, and methacrylamido; and
   b) recovering said free radical or visible light curable acid-containing polymers from the reaction mixture.

24. The method of claim 23 wherein the free radical polymerizable vinyl residue is selected from the group consisting of acrylate, methacrylate, acrylamido, methacrylamido, and combinations thereof.

25. The method of claim 1 wherein the oxazoline or a 5,6-dihydro-1,3oxazine is 4,5-dihydrooxazole or 5,6-dihydro-4H-1,3-oxazine.

26. The method of claim 16 wherein the oxazoline or a 5,6-dihydro-1,3oxazine is 4,5-dihydrooxazole or 5,6-dihydro-4H-1,3-oxazine.

* * * * *

UNITED STATES PATENT AND TRADEMARK OFFICE
CERTIFICATE OF CORRECTION

PATENT NO. : 6,512,054 B2
DATED : January 28, 2003
INVENTOR(S) : Bill M. Culberston and Scott R. Schricker It is certified that error appears in the above-identified patent and that said Letters Patent is hereby corrected as shown below:

<u>Title page, Item [54] and Column 1, Line 1,</u>
Please delete "RACDICAL" and insert -- RADICAL --.

<u>Column 11,</u>
Line 45, please delete

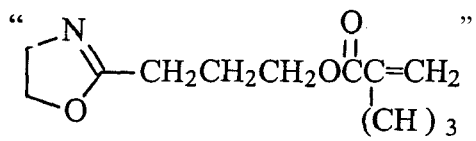

and insert

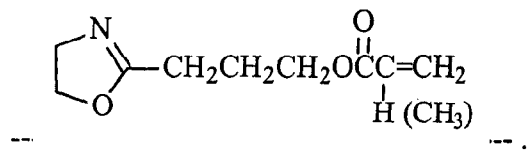

Signed and Sealed this

Twenty-fourth Day of June, 2003

JAMES E. ROGAN
*Director of the United States Patent and Trademark Office*